United States Patent
Rothman

(10) Patent No.: US 6,978,183 B2
(45) Date of Patent: Dec. 20, 2005

(54) SYSTEM AND METHOD FOR COOLING THE CORTEX TO TREAT NEOCORDICAL SEIZURES

(75) Inventor: Steven M. Rothman, Clayton, MO (US)

(73) Assignee: The Washington University, St. Louis, MO (US)

(*) Notice: Subject to any disclaimer, the term of this patent is extended or adjusted under 35 U.S.C. 154(b) by 304 days.

(21) Appl. No.: 09/905,715

(22) Filed: May 4, 2001

(65) Prior Publication Data

US 2003/0028229 A1 Feb. 6, 2003

(51) Int. Cl.⁷ .................................. A61F 7/00
(52) U.S. Cl. .................. 607/99; 607/109; 600/544
(58) Field of Search .................. 607/98, 99, 109, 607/110, 96, 113; 600/377, 393, 544

(56) References Cited

U.S. PATENT DOCUMENTS

| | | | | |
|---|---|---|---|---|
| 5,311,876 A | * | 5/1994 | Olsen et al. | 600/544 |
| 5,857,978 A | * | 1/1999 | Hively et al. | 600/544 |
| 6,248,126 B1 | | 6/2001 | Lesser et al. | 607/113 |
| 6,304,775 B1 | * | 10/2001 | Iasemidis et al. | 600/544 |
| 6,337,997 B1 | * | 1/2002 | Rise | 607/45 |
| 6,473,639 B1 | * | 10/2002 | Fischell et al. | 600/544 |

OTHER PUBLICATIONS

Hill, Matthew W., et al., Rapid Cooling Aborts Seizur–Like Activity in Rodent Hippocampal–Entorhinal Slices, Epilepsia, 41(10):1241–1248, 2000.*

* cited by examiner

Primary Examiner—Roy D. Gibson
(74) Attorney, Agent, or Firm—Blumenfeld, Kaplan & Sandweiss, P.C.

(57) ABSTRACT

A manually activated Peltier device was placed in direct contact with a cortical slice. Seizures terminated within seconds of the onset of cooling, sometimes preceding a detectable drop in temperature measured near the top of the slice. Activation of the Peltier did not stop seizures when slices were no longer in direct physical contact with the device, indicating that this was not a field effect. When cooling was shut off and temperature returned to 33° C., the bursting sometimes returned, but a longer term suppressive effect on seizure activity could be observed. In two experiments, a custom computer program automatically detected seizure discharges and triggered a TTL pulse to activate the Peltier. In these experiments the Peltier automatically terminated the slice bursting in less than four seconds. When the Peltier device was placed in contact with the normal, exposed cortex of a newborn pig, we found that the cortical temperature rapidly decreased from 36° C. to as low as 26° C., at a depth of 1.7 mm below the cooling unit. Therefore, local cooling may rapidly terminate focal paroxysmal discharges and might be adapted for clinical practice.

1 Claim, 17 Drawing Sheets

0.3 mV
6° C
10 S

SYSTEM AND METHOD FOR COOLING THE CORTEX TO TREAT NEOCORDICAL SEIZURES

BACKGROUND

The invention generally relates to systems and methods for treating seizures and, in particular, to a method of cooling the cortex using a Peltier cell to abort intractable focal neocortical epilepsy.

Well over half of the resections for the treatment of intractable seizures are directed at temporal lobe epilepsy (1). In Olivier's series of 560 operations for control of epilepsy, 74% were on temporal lobes, 11% on frontal lobes, 1.3% on central regions, 0.9% on parietal lobes, and 0.8% on occipital lobes (2). The other 12% were multilobar resections (2.5%) and corpus callosotomies (9.5%). This may be related to the relatively high epileptogenicity of the mammalian temporal lobe, but may also reflect the greater ease in localizing and resecting epileptic foci in the temporal lobes (3). The surgical therapy of intractable neocortical epilepsy is still suboptimal for many children and adults. There are at least three reasons for this. First, it can be difficult to identify the exact site(s) responsible for seizure generation. Second, the extent of the required resection is not easy to anticipate. Third, removal of the seizure focus might produce an irreversible neurological deficit not predicted from presurgical neuropsychological or radiological evaluation. The complexity of functional localization is especially serious in children, who cannot undergo direct cortical mapping under local anesthesia (4).

We have, therefore, become interested in exploring alternative techniques to address these problems related to the surgical therapy of the neocortical epilepsies. We were aware of a substantial literature in neurophysiology and experimental neurology documenting the ability of focal cooling to reversibly inactivate the mammalian cortex (5, 6). We have also reviewed earlier research demonstrating that focal cooling can diminish paroxysmal activity in vivo (7, 8, 9).

In particular, we have become interested in exploring the possibility that focal cooling might enhance the surgical therapy of neocortical epilepsy. There is already a substantial literature in neurophysiology and experimental neurology demonstrating the ability of cooling to reversibly inactivate the central nervous system[103,104]. The precise mechanism(s) mediating the functional effects of cooling are not fully understood, but in vitro cellular reports have demonstrated that cooling can interfere with normal synaptic transmission and voltage-gated ion channels[105,106,107].

Clinicians have recognized a relationship between seizures and temperature for centuries and there are a few modern accounts of terminating seizures in patients by temperature reduction[108,109]. There are also several in vivo and in vitro studies demonstrating a slow reduction in paroxysmal activity in models of epilepsy after gradual cooling[110,111,112,113]. The ready availability of small thermoelectric (Peltier) cooling devices, initially developed for the computer industry, makes cortical cooling an especially attractive option for investigation (see FIG. 9A, below)[114].

SUMMARY OF THE INVENTION

It is an object of this invention to take advantage of the fact that rapid cooling can terminate seizure-like discharges in the hippocampal-entorhinal slice preparation[15]. It is a further object of the invention to use the same technique in a new model of focal epilepsy to control seizures in vivo.

We wanted to try new, small Peltier devices to determine whether we could rapidly and reversibly inactivate seizure discharges, since the previous work on focal cooling and epilepsy had shown the effects of relatively slow onset cooling (10). For our initial experiments we have used an in vitro seizure model. While this is not as realistic as in vivo epilepsy, it eliminated some of the practical problems that are encountered with behavioral seizures and made it easier for us to concentrate on optimizing temperature control in initial experiments.

Our experiments have shown that it is possible to employ a Peltier device to rapidly cool slices and terminate paroxysmal discharges. We believe it will become possible to combine this technique with implantable grids that will allow us to identify site(s) responsible for the origin of focal seizures and ascertain the functional consequences of ablating these sites. Our ultimate hope is a permanently implantable device that will anticipate a clinical seizure and activate cooling prior to a behavioral event.

BRIEF DESCRIPTION OF THE DRAWINGS

FIG. 2A-CONTROL. Arrow indicates onset of 35 second normothermic seizure recorded in the dentate granule cell layer. FIG. 2B-COOLING. A seizure in the same slice was terminated after seven seconds by cooling. FIG. 2C-RECOVERY. When normothermic, the same slice resumed generating seizure-like discharges, but they were briefer than before cooling. V: voltage; T: temperature.

FIG. 5A illustrates a control at 32° C. As observed by others, cooling reduced the response (see FIGS. 5B AND 5C), which gradually returned with warming (see FIGS. 5D, 5E AND 5F). Temperature measurements were recorded at the slice surface with a thermocouple.

V: extracellular voltage record; On: TTL pulse triggered by software. Voltage scale only applies to upper trace.

Figure 7A:
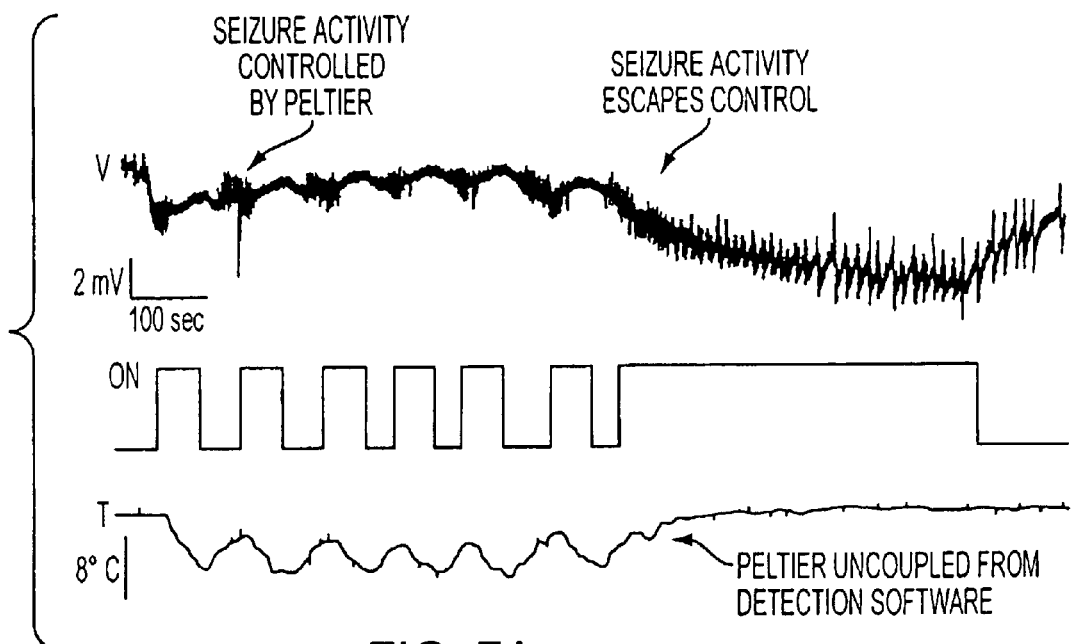
Figure 7B:
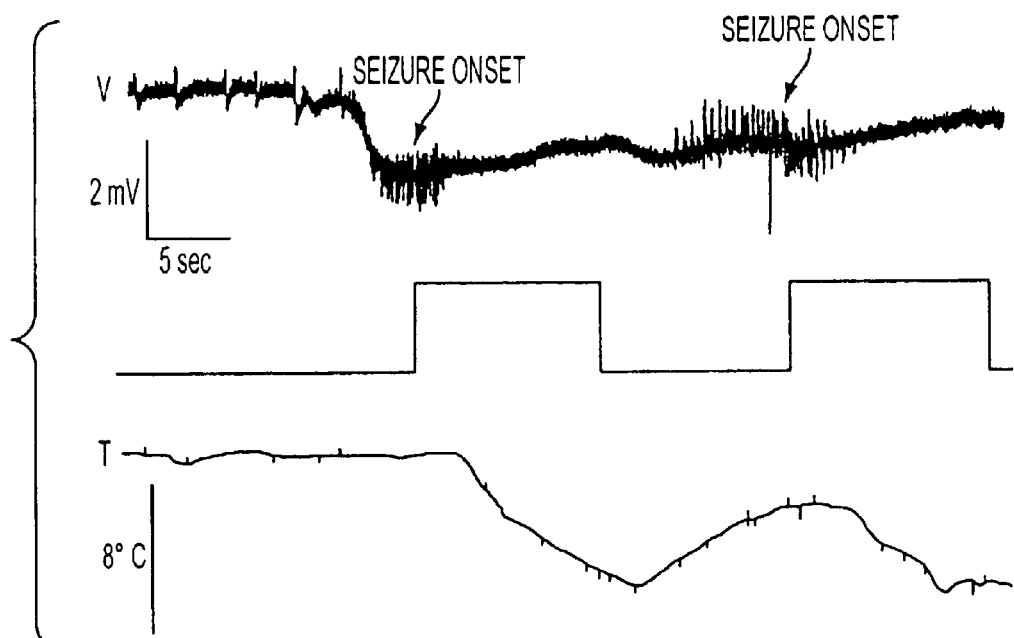

FIGS. 7A–7B. Computerized seizure detection software activates the Peltier device, cools the slice, and suppresses 4-AP—induced paroxysmal activity in mouse entorhinal cortex. A. Upper FIG. 7A shows automatic cooling terminating six seizures. When the Peltier device was disconnected, the detection program continued to put out a continuous TTL signal because the bursting was continuously present. B. Lower FIG. 7B shows the first two seizures (line over start of voltage trace in A) at an expanded time scale. The Peltier device was not activated at the onset of the spiking, but only when the seizure frequency and amplitude exceeded threshold settings (arrows). The temperature trace shows that seizure termination preceded a detectable reduction in temperature near the top of the slice. V: extracellular voltage in entorhinal cortex; On: TTL output to Peltier device; T: temperature.

Figure 8:
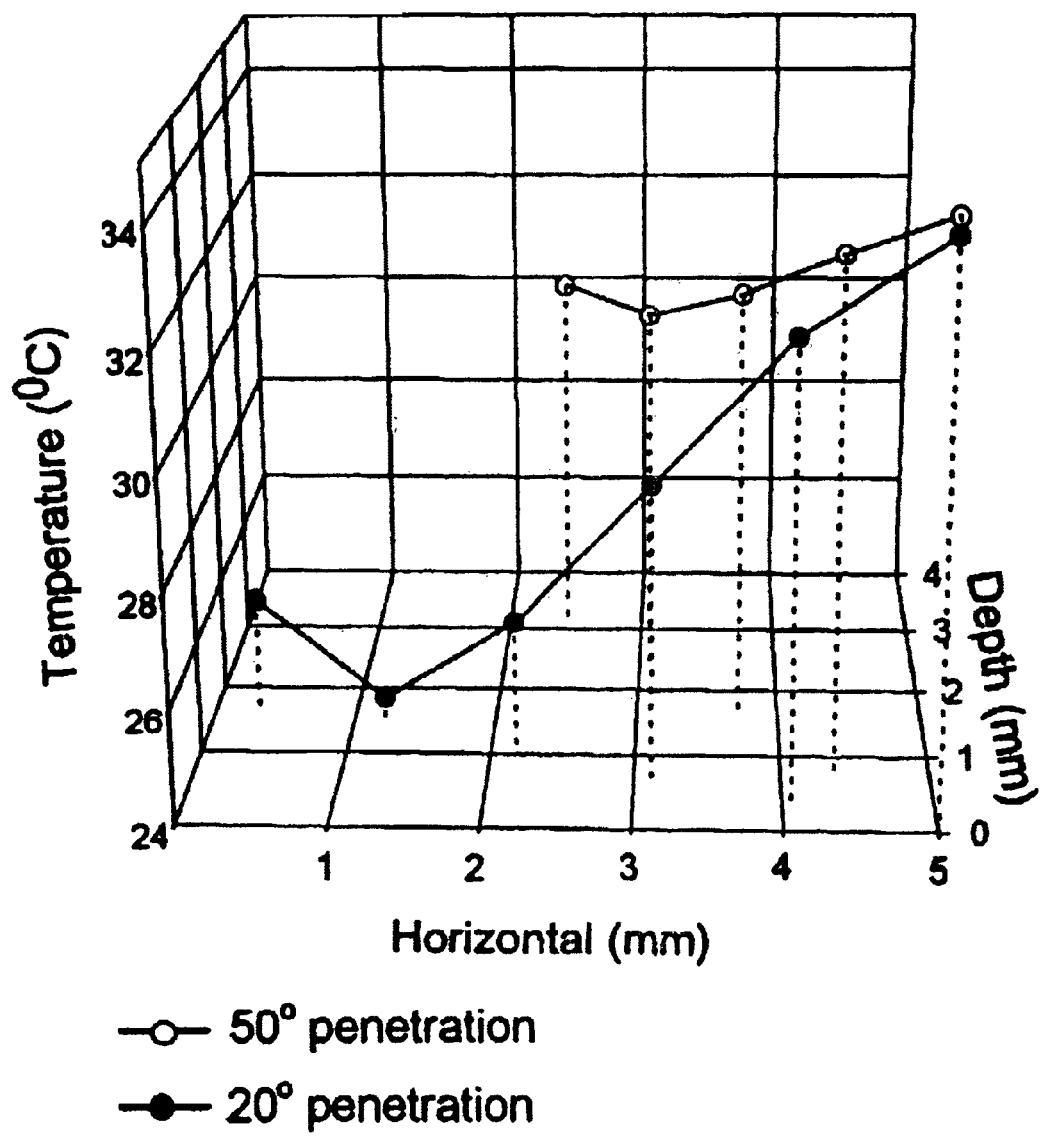

FIG. 8. Temperature distribution in newborn pig neocortex when thermocouple was advanced into the brain at two different angles (20° and 50°) at the edge of the Peltier device. At the steeper angle, the thermocouple did not get as close to the center of the Peltier device, which was 10 mm wide, and the minimum temperature was, therefore, lower at the shallower angle (24.6° C. vs 30.6° C.).

Figure 9A:
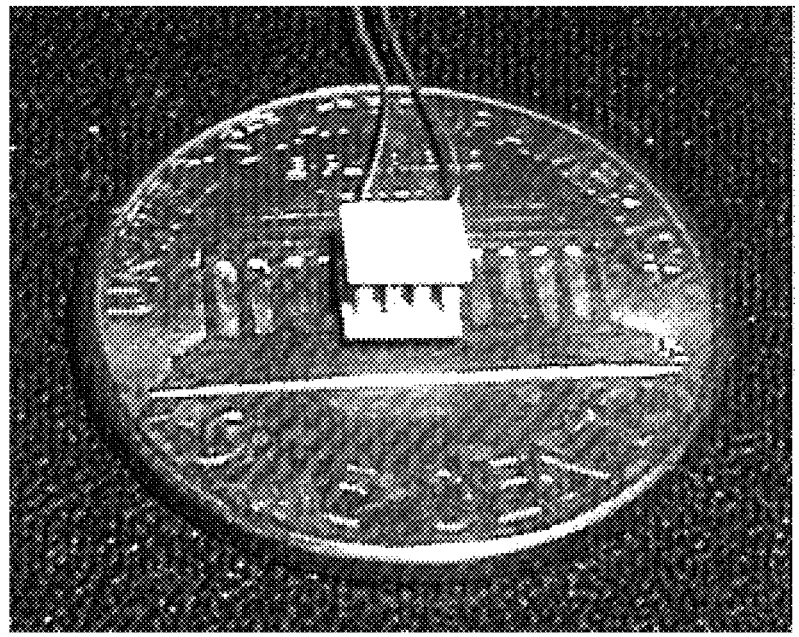
Figure 9B:
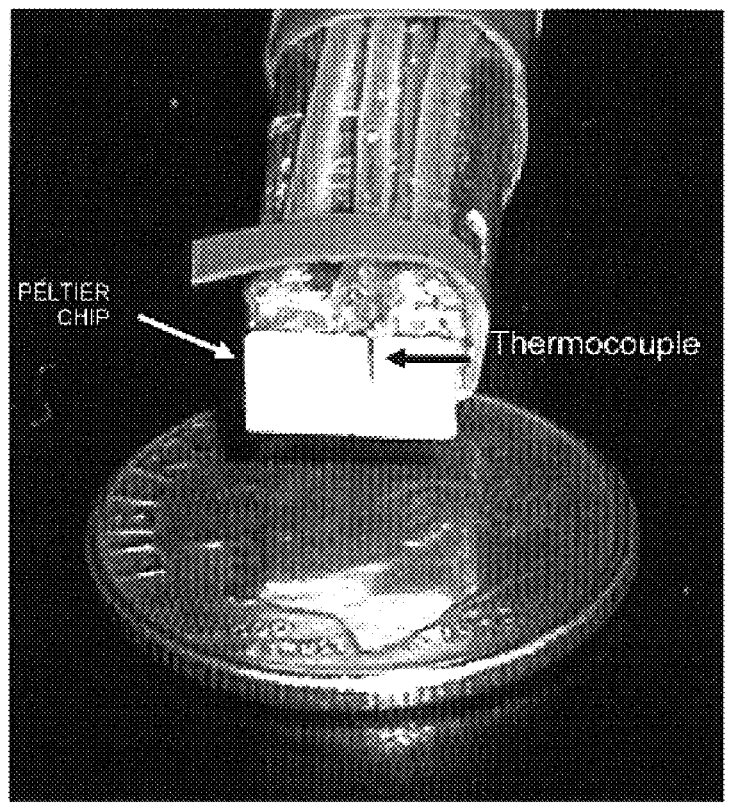

FIGS. 9A–9B. Examples of the Peltier devices used for neocortical cooling. FIG. 9A. The individual Peltier chips used in these experiments are composed of two ceramic wafers connected by seven semiconductors. FIG. 9B. Two chips were glued to the end of a copper rod that provided a convenient holder and efficient heat sink. Temperature at the brain—Peltier interface was monitored by a thermocouple (black arrow). The tubing on the top of the rod insulates the wires serially connecting the Peltier chips to a DC power supply.

Figure 10:
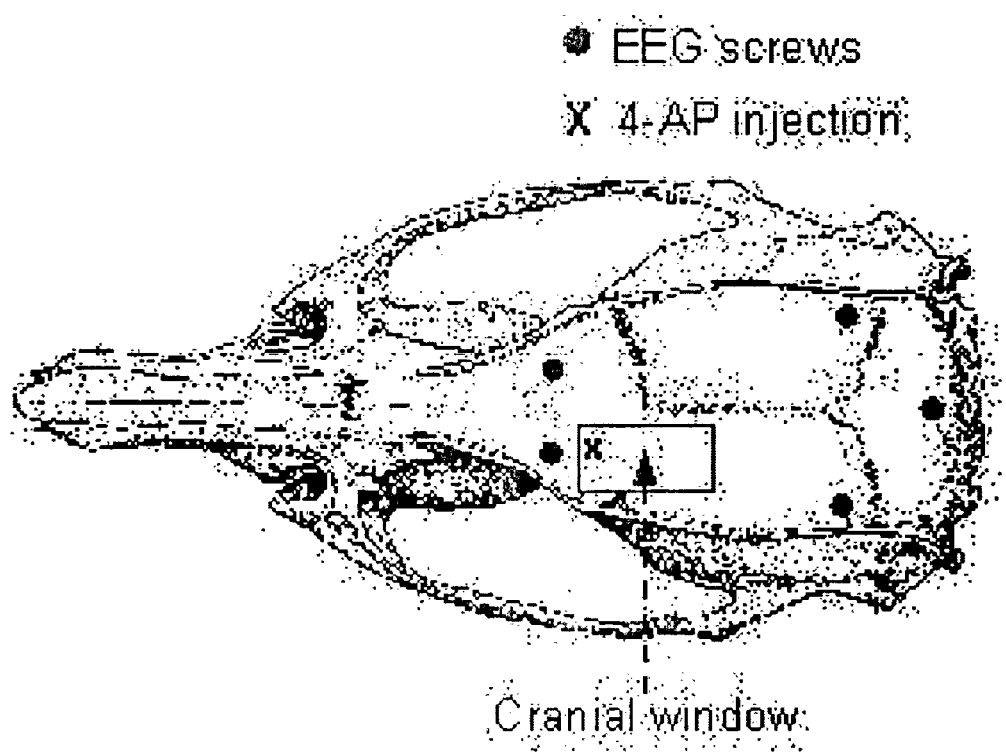

FIG. 10. Cranial window and electrode placement. FIG. 10 shows location of the 4 screw electrodes used for EEG recording and the grounding electrode. The cranial window overlays the motor cortex, the site of the 4-AP injection.

Figure 11A:
Figure 11B:
Figure 11C:
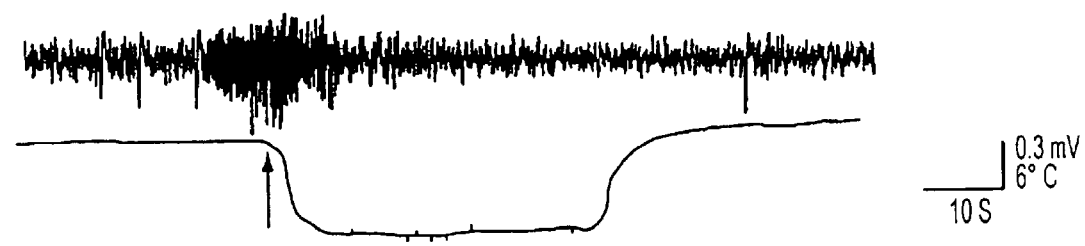

FIGS. 11A–11C. Examples of 4-AP induced neocortical seizures. FIG. 11A. Control seizure lasting ninety seconds. FIG. 11B. Activating the Peltier device did not alter the course of a ten second seizure when the device was not in direct contact with the cortical surface. FIG. 11C. Direct cortical cooling by the Peltier device 8 seconds after onset terminated a seizure within 9 seconds. The temperature reduction in FIGS. 11B AND 11C differ because the Peltier surface was cooled from room temperature (about 25° C.) down to 20° C. in FIG. 11B, and from brain surface temperature (about 34° C.) to 20° C. in FIG. 11C D1, D2. Start and end of seizure shown in C., at an expanded time base.

Figure 12A:
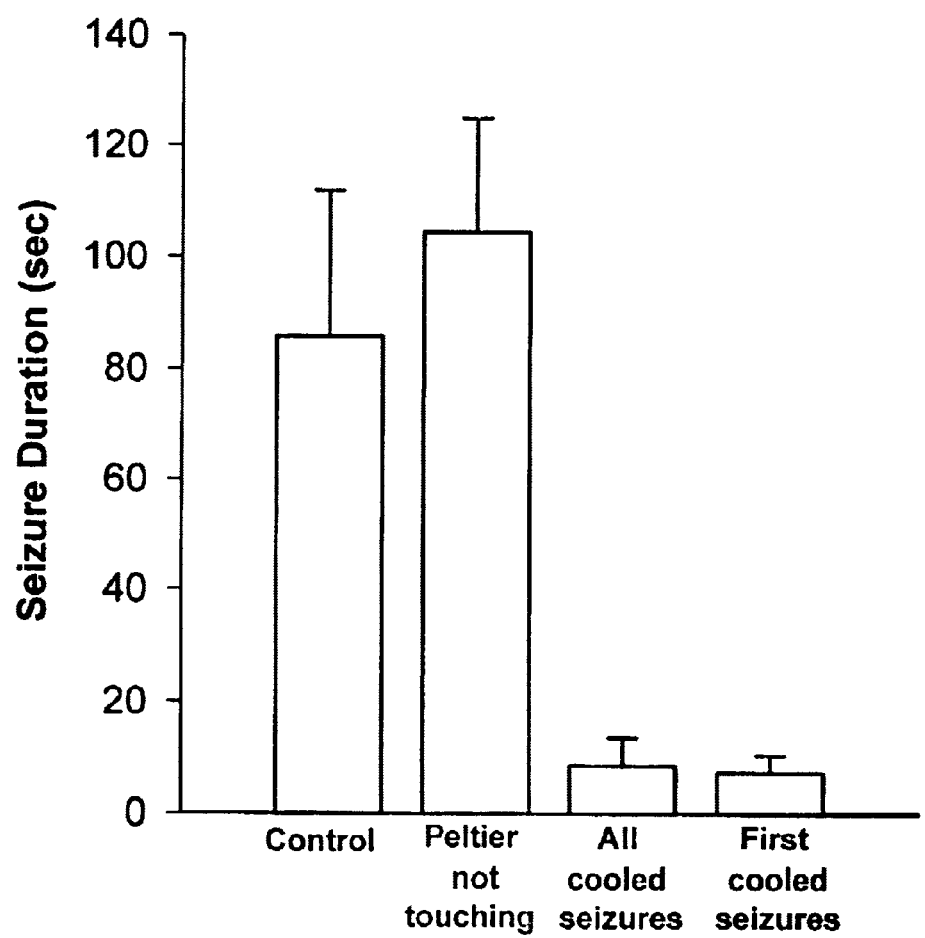
Figure 12B:
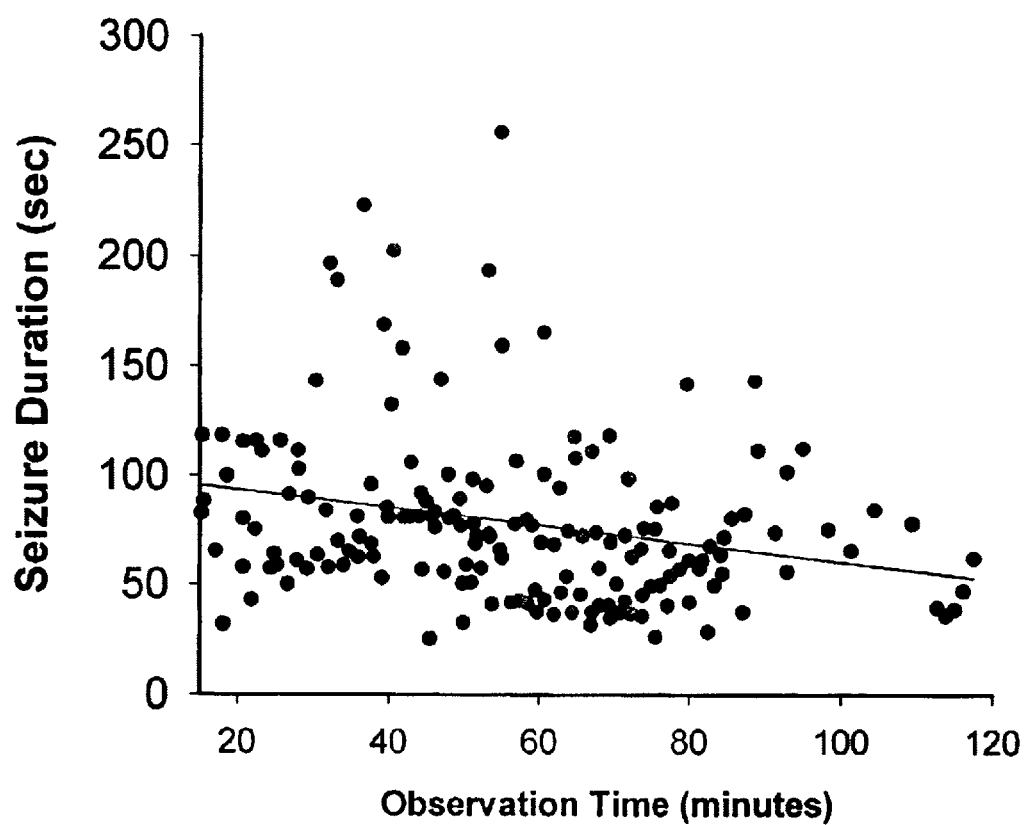
Figure 12C:
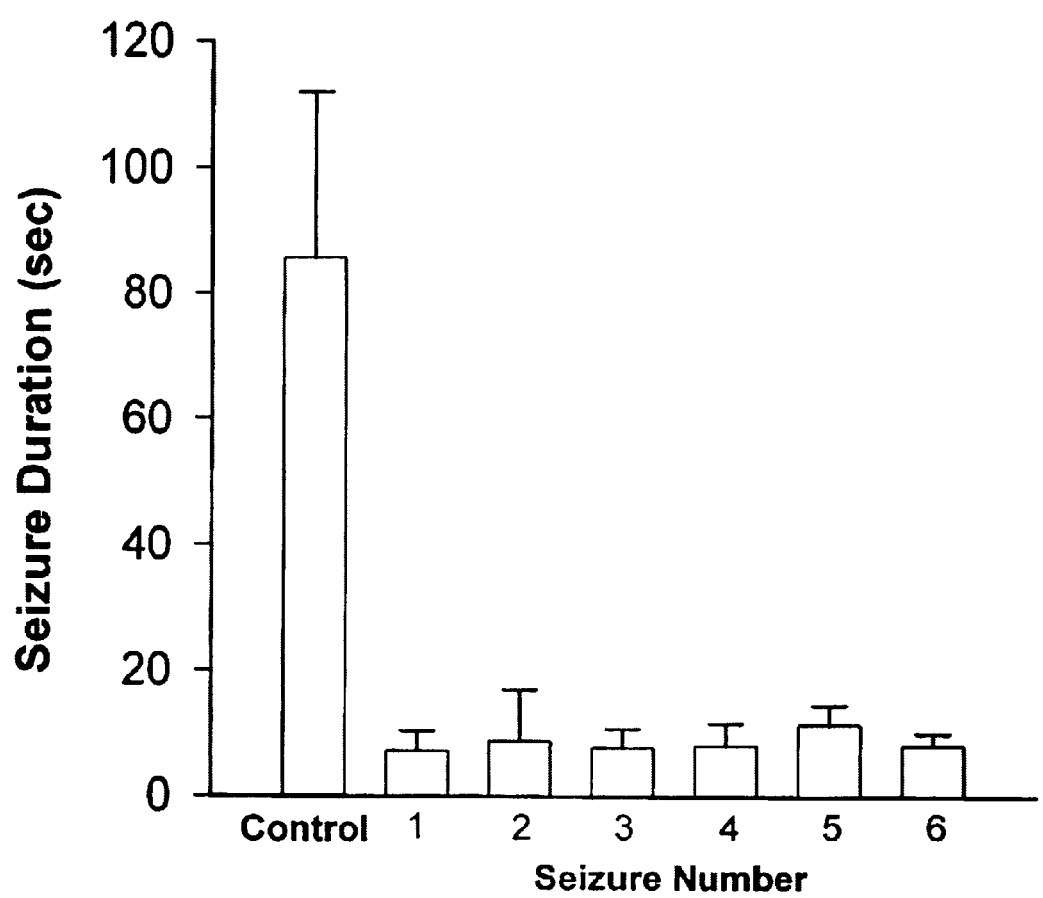

FIGS. 12A–12C. Cortical cooling significantly reduces the duration of seizures. FIG. 12A. Cooling shortens the duration of the entire group of cooled seizures, as well as the first cooled seizure in each animal. Activation of the Peltier had no effect on seizure duration if the device did not directly contact the cortex. a, b: different from c and d ($p<0.001$, Tukey), but not each other; c, d: different from a and b ($p<0.001$, Tukey), but not each other.

FIG. 12B. Control, uncooled seizure durations decreased over a two hour observation period, but were still significantly longer than cooled seizures (see text). FIG. 12C. Control seizures were longer than first through sixth cooled seizure groups, respectively ($p<0.001$, Tukey). However, the durations of the first through sixth cooled seizure groups were not significantly different from each other.

Figure 13A:
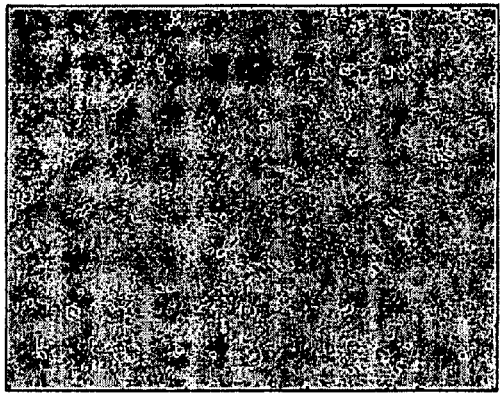
Figure 13B:
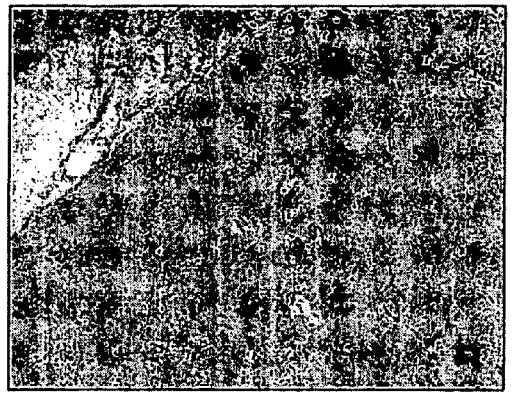
Figure 13C:
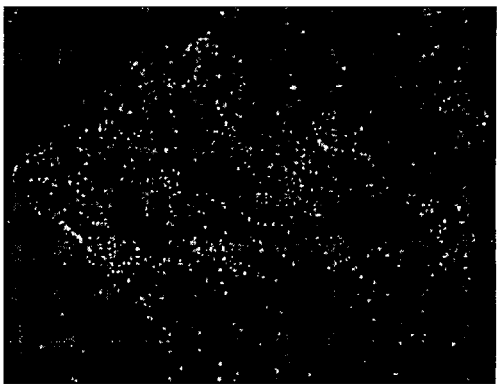
Figure 13D:
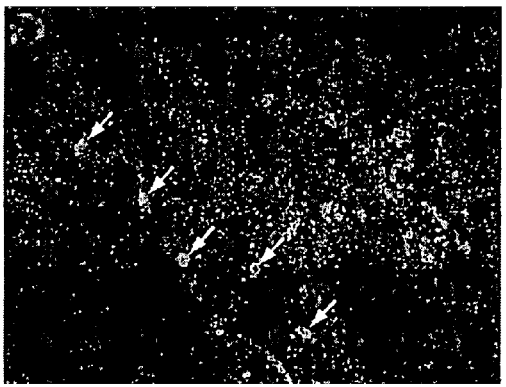

FIGS. 13A–13D. Nissl and TUNEL staining reveal no pathological effects of cortical cooling. FIG. 13A. Nissl stained frontal neocortex after sham surgery shows normal anatomy. FIG. 13B. Section from animal that had 4-AP injection followed by Peltier cooling (two, 2-minute periods) appears identical. FIG. 13C. No TUNEL positive cells (green fluorescence) are evident in section from 4-AP injected and Peltier—cooled animal. FIG. 13D. Direct contact with the cooling pipe caused extensive cortical damage and the appearance of many TUNEL-positive cells (arrow heads). The faint red fluorescence in FIGS. 13C AND 13D comes from the propidium iodide that was added to counterstain nuclear DNA and verify that TUNEL staining localized to nuclear DNA. Legend: 100 $\mu$m, FIGS. 13A–13D.

Figure 14:
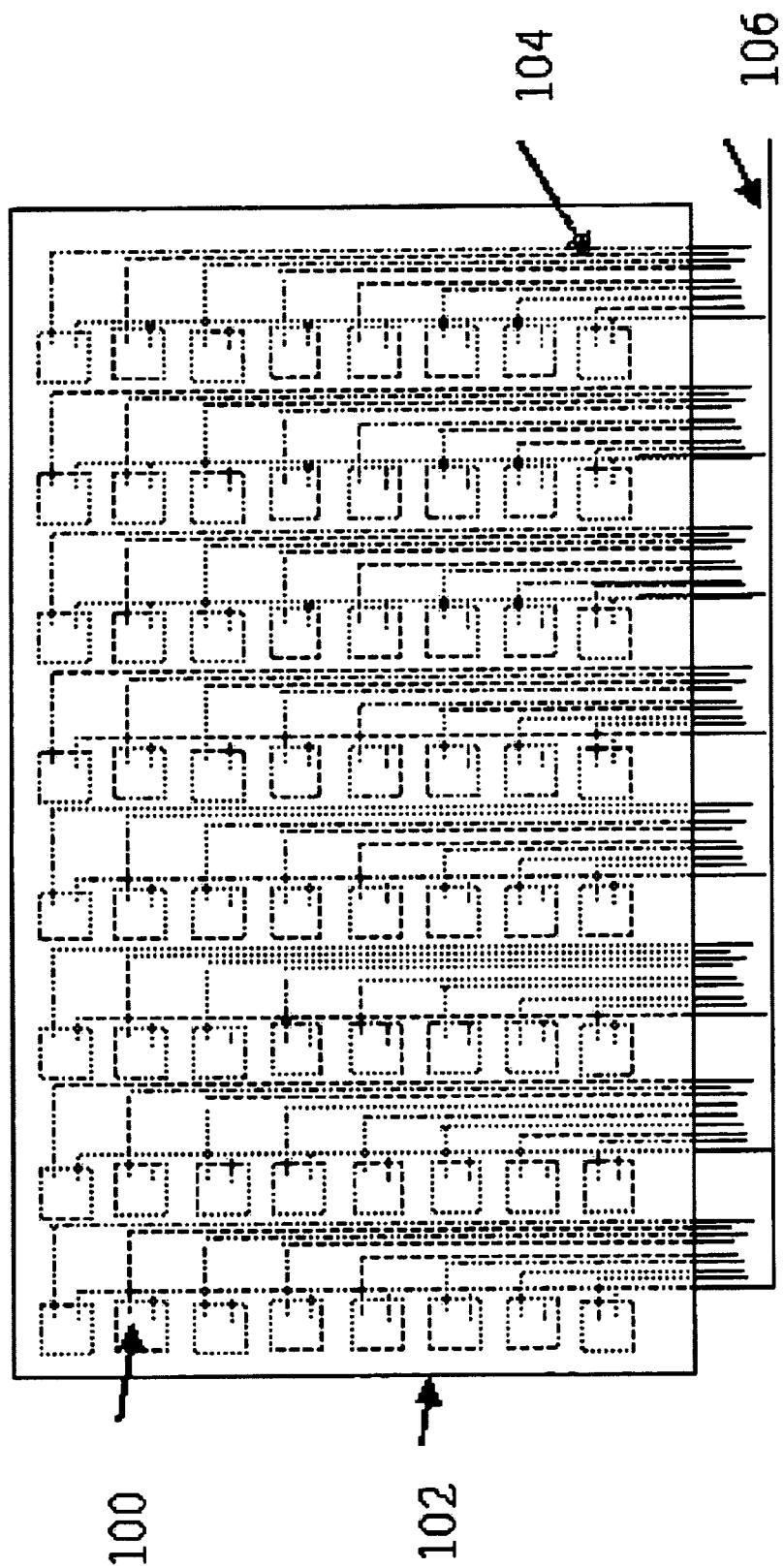

FIG. 14. FIG. 14 shows the embodiment of the present invention wherein a an array of the Peltier devices in an implantable subdural grid adjacent to recording electrodes.

DETAILED DESCRIPTION OF PREFERRED EMBODIMENTS

Methods

Slice Preparation

Figure 1:
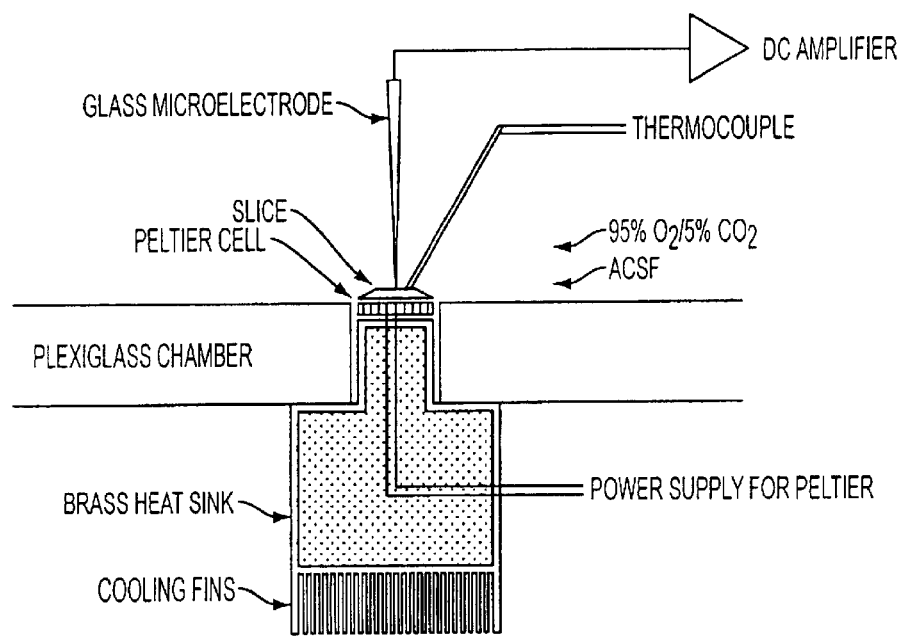
FIG. 1A. Cross sectional view of the modified chamber used to cool slices with the Peltier device. The slice was in direct contact with the Peltier device, which was glued to a brass heat sink attached to the base of the chamber.

Slices that included both the hippocampus proper and entorhinal cortex were prepared according to the method of Barbarosie and Avoli (11). We used juvenile, male rats or adult, male, CD-1 mice, which were anesthetized with halothane and then decapitated. Our protocols were approved by the Washington University Animal Studies Committee. After the brains were carefully removed, they were briefly immersed in ice-cold artificial cerebrospinal fluid (ACSF) containing (in mM): 124 NaCl, 2 KCl, 1.25 $KH_2PO_4$, 2 $MgSO_4$, 2 $CaCl_2$, 26 $NaHCO_3$, and 10 glucose. The ACSF was constantly bubbled with a 95%$O_2$/5% $CO_2$ mixture. While the brain rested on the dorsal surface on an ACSF-dampened piece of filter paper, the cerebellum and brain stem were removed without touching either temporal lobe. The brain anterior to the optic chiasm was removed with a single coronal cut, so that the frontal surface could be placed against an agarose block in the vibratome pan, while the brain remained on its dorsal surface (FIG. 1A). After the pan was placed into the vibratome (Pelco 1050 vibratome series 1000, St. Louis, Mo.) and filled with ice-cold, oxygenated ACSF, the vibratome's well was filled with ice water to cool the outside surface of the pan. Horizontal slices of 600 $\mu$m were individually cut in 90 to 120 seconds at the maximum blade vibration amplitude. After the hemispheres had been separated, each half-slice was transferred to either the recording chamber or a separate holding chamber. In our holding chamber, slices lay on a piece of ACSF-saturated filter paper underneath humidified 95%$O_2$/5% $CO_2$. Experiments were begun after the slices had recovered for an hour.

Electrophysiology

For these experiments we modified a commercial interface chamber (Medical Systems, Greenvale, N.Y.) so that the hippocampal—entorhinal slice could be placed on a small piece of lens paper in direct contact with the surface of a Peltier device measuring 5×5×2.4 mm (Melcor, Trenton, N.J.). We colored the lens paper to improve light contrast and make it easier to identify the laminations in the slice. The Peltier device was fitted into the chamber so that its upper surface was flush with the plexiglass on which the slice would normally rest (FIG. 1A). The bottom surface of the Peltier was glued to a large, brass heat sink that was attached to the center of the slice chamber. This allowed heat to quickly dissipate when the Peltier was activated. Humidifed gas (95%$O_2$/5% $CO_2$) flowed over the slice, which was perfused with oxygenated ACSF flowing at 2–4 ml per minute. After the slice temperature reached 33° C., we induced seizures by changing to modified ACSF containing 4-aminopyridine (4-AP; 50 µM). The Peltier device was connected to a DC power supply that could be manually activated or automatically gated by a computer (see below). For most of each experiment, the Peltier remained off and temperature was held at about 33° C. by the resistive heating coils in the slice chamber. When a seizure was detected, the Peltier was turned on to rapidly cool the slice. Current flow in the Peltier was 0.6–0.8 A. Slice temperature was directly monitored with a thermocouple inserted into a 33 g needle (Hyp-0, Omega, Stamford, Conn.). The thermocouple output was read by a temperature controller (CN1000TC, Omega), whose output was connected to our data acquisition system.

We fabricated microelectrodes from 1.2 O.D./0.68 I.D. (mm) microfiber-filled borosilicate glass tubing (W.P.I., Sarasota, Fla.). Their impedances were 4 to 6 MΩ when filled with ACSF. Field potentials were recorded from either the medial portion of the entorhinal cortex, $CA_3$ pyramidal cell layer, or the granule cell layer of the dentate. Signals were fed to conventional DC amplifiers (model M-707 W.P.I., Sarasota, Fla.; model 1600, A-M Systems, Carlsborg, Wash.; or Axoclamp-2A, Axon Instruments, Foster City, Calif.) and filtered at 1 kHz. Amplifier output was digitized at 1 KHz using an analog to digital converter and commercially available software (Digidata 1200 and Axoscope 7, Axon Instruments). In some experiments we used a "Hum Bug" (Quest Scientific, North Vancouver, Canada) to remove 60 Hz harmonics. The digital traces were then analyzed visually to determine seizure frequency and duration. In our initial experiments, we recorded to a tape recorder (Biologic, Claix, France) and digitized data off line using identical methods.

We developed our own computer program using Axobasic (Axon, Foster City, Calif.) and Microsoft Basic to detect seizures and activate the Peltier device. Signals were filtered at 1 KHz, amplified (100×), and then digitized (1 MHz). We then measured the difference in the absolute value of the processed signal at the beginning and end of successive 20 msec intervals. When this difference signal repeatedly exceeded a threshold value, usually set at 0.5 V (corresponding to 5 mV for the unamplified signal), a TTL signal activated the Peltier device for 5 sec windows, that were continually updated as long as the seizure persisted. The program was typically set so that the difference signal had to exceed threshold at a frequency between 5 and 20 Hz and required at least one second to trigger a TTL pulse. Although this program did not directly sample spike frequency or amplitude, it effectively discriminated noise from signals that fit our criteria for seizure-like discharges. We would be happy to provide a compiled version of the program or source code to interested readers.

Temperature Measurements

We used two anesthetized newborn piglets to determine whether our Peltier device could cool a small region of the normally perfused cortex of a large mammal. The piglets had been used immediately before our experiments for platelet adherence studies that required the insertion of a closed cranial window over the motor cortex (12, 13). While the animals remained ventilated under isoflurane anesthesia, the windows were removed, leaving the underlying cortex exposed. A Peltier device (10×5×2.4 mm), glued to the end of a brass rod that served as both probe holder and heat sink, was allowed to touch the cortical surface. A 33 g thermocouple (Hyp-0, Omega), mounted on a micromanipulator, was inserted just lateral to the Peltier and advanced in fixed steps, so that temperature at increasing distance from the Peltier could be measured.

Data Analysis

All statistical values are presented as mean±standard deviation. The "n" for statistical analysis was the number of seizures. Appropriate statistical tests were carried out with commercially available software (SigmaStat, Jandel Corporation, San Rafael, Calif.).

Results

Cooling and Seizure—Like Discharges

Figure 2A:
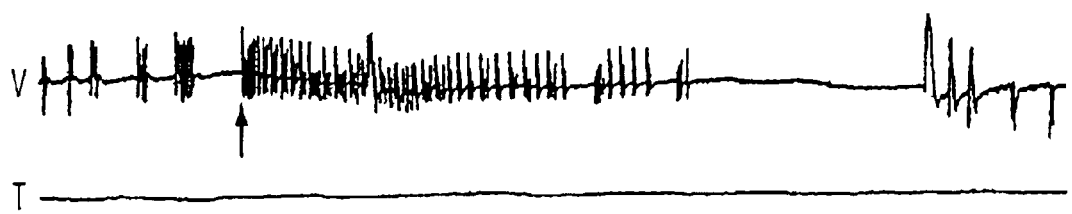
FIGS. 2A–2C. Cooling suppresses seizure-like discharges in the dentate granule cell layer of a slice exposed to 4-AP (50 $\mu$M).

In our previous slice work, we defined a seizure as a series of rapid, synchronous electrical oscillations of at least ten second duration, from the onset of tonic firing to the end of the clonic phase (14) (FIG. 2A). These seizures typically developed within two hours of perfusing modified ACSF. Activity gradually built in intensity with interictal bursts and seizures becoming more frequent, larger in amplitude, and often longer in duration. This increase in intensity typically reached a plateau in 30 to 90 minutes. After this point many slices entered a pattern of high-intensity interictal bursting without any seizures. This evolution has been well documented by Barbarosie and Avoli, who also demonstrated that seizure activity could be restored with a microlesion to the Schaffer collateral pathway (11).

In our previous study of 31 slices exposed to low $Mg^{2+}$ ACSF or 4-AP (50 µM), seizures almost always lasted over 35 seconds (14). In an initial set of cooling experiments, we did not allow individual seizure discharges to continue, since we wanted to determine whether we could rapidly terminate seizures after activation of the Peltier device. We manually triggered the Peltier device after spontaneous seizures were observed in 8 slices exposed to 4-AP. In each of these slices, activation of the Peltier device stopped seizures within a few seconds. The temperature dropped as much as 12° C. in some of these slices with activation of the Peltier. We frequently noticed a DC shift coincident with cooling, but an identical DC shift was sometimes seen during normothermic bursting. When the cooling was discontinued, the seizures frequently recurred. However, control slices cooled in absence of 4-AP never demonstrated hyperexcitability, so this can be at least partly attributed to the continued presence of convulsant.

Figure 2B:
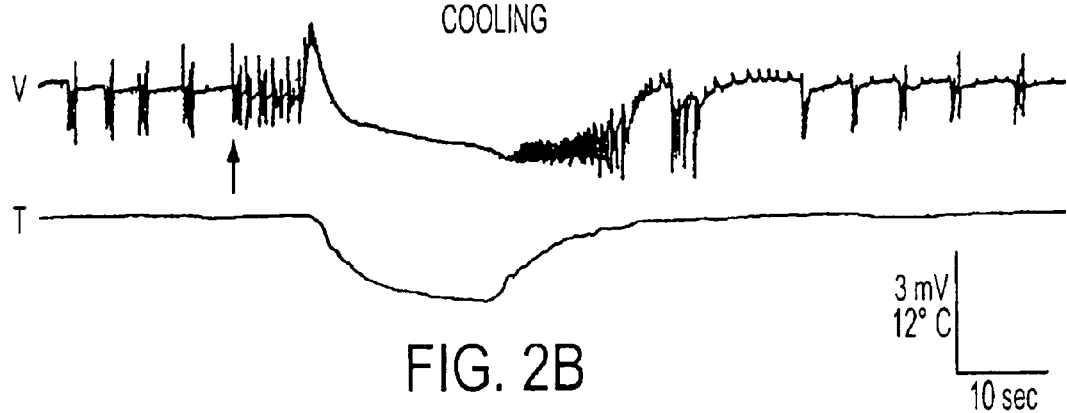
Figure 2C:
Figure 3:
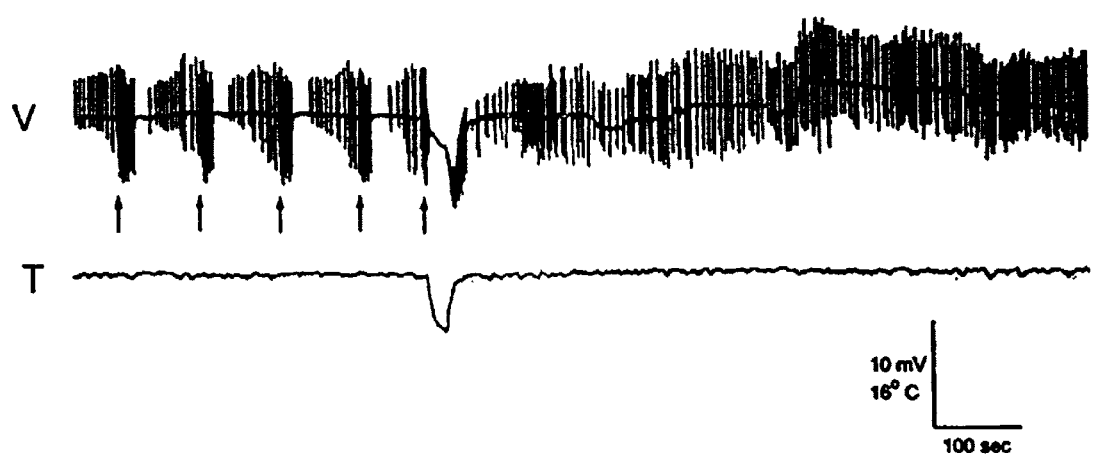
FIG. 3. Effect of cooling observed on a slower time scale. Four normothermic seizures were observed in a 4-AP exposed slice (arrows). At the onset of the fifth seizure, the slice was cooled, resulting in seizure termination. There was a rebound hyperexcitability during the immediate rewarming phase. While there were interictal bursts for the next 11 minutes, there were no seizure-like discharges. This relative refractory period corresponds to the reduced evoked field potentials observed for at least ten minutes after slice cooling (see FIG. 5). V: voltage; T: temperature.

We then compared the duration of control and cooled seizures in another six slices exposed to 4-AP, so that we could assess the effect of cooling in the same slices in which we had data on normothermic seizures. Prior to activation of the Peltier device, seizure duration was 35.9±12.6 seconds (24 seizures)(FIG. 2A). When cooling was initiated at the onset of individual seizures, usually after about five seconds, the seizures were shortened to 7.3±1.7 seconds (18 seizures; p<0.05, compared to control)(FIG. 2B). While this effect is dramatic, it is still an underestimate of the magnitude of the cooling effect, since we have included the five seconds prior to initiation of the cooling in our measurement of cooled seizure duration. Interestingly, during the recovery period, normothermic seizure duration increased to only 14.2±4.0 seconds (11 seizures; p<0.05 compared to both control and cooling by Student-Newman-Keuls test) and seizures failed to recur in three of the six slices used for this set of experiments, suggesting that cooling had an effect that outlasted the period of Peltier activation (FIGS. 2C and 3). Other control experiments (see below) indicate that slice deterioration cannot account for the briefer and less frequent seizures observed later in our experiments.

Figure 4:
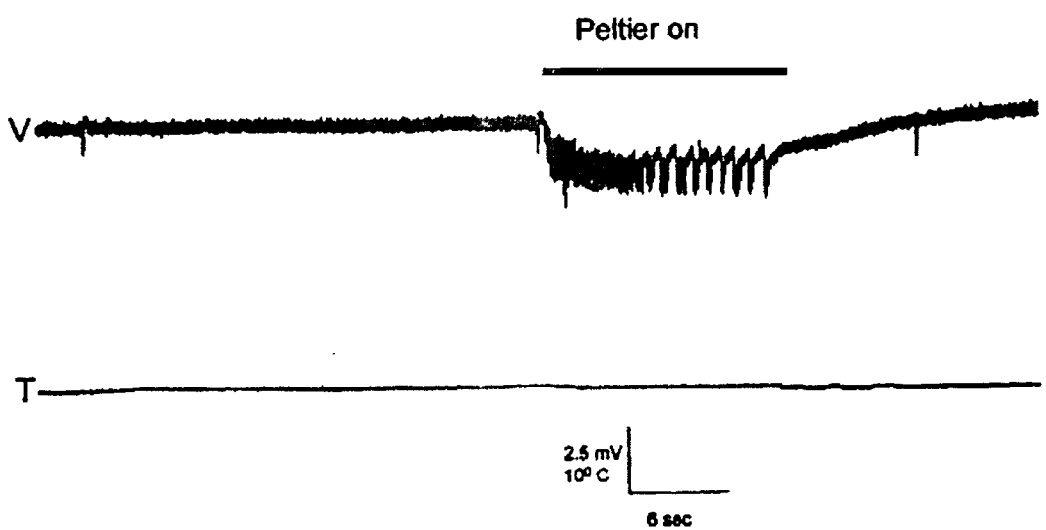
FIG. 4. Seizure termination is not due to the Peltier electric field. A piece of styrofoam was inserted between the slice and the Peltier. When the Peltier was activated after onset of a spontaneous seizure, the slice failed to cool and the seizure did not terminate quickly (compare temperature trace with trace in FIG. 2B). V: dentate voltage; T: temperature.

We were concerned that seizure control might be an effect of the electrical field produced by current flow in the Peltier device. We, therefore, determined if activation of the Peltier could terminate seizures if the slice was not in direct physical contact with the chip. In one set of experiments, the slice was thermally, but not electrically, isolated from the cooling chip with a thin piece of styrofoam. When seizures were induced under this condition, activating the Peltier device had no obvious influence on slice bursting and there was no effect on temperature recorded with a thermocouple inserted into the top of the slice (n=2) (FIG. 4). We also examined the effect of bringing a Peltier device as close as possible to the top of slice (about 1 mm) and recording pipette, without making direct physical contact (n=2). In order to do this, we approached the slice from the side, with the Peltier mounted on a brass rod to serve as a both holder and heat sink. Under these conditions, seizures lasted 27.6±10 seconds with the Peltier off and 29.6±10.6 seconds when the Peltier was activated shortly after seizure onset. During the recovery period, seizure duration was 24.1±8.4 seconds (8 seizures for each condition; p>0.5). It, therefore, is unlikely that the electrical field produced by current flow in the Peltier device is responsible for seizure termination. These results incidentally demonstrate the minimal reduction in seizure duration over the time period involved in our experiments.

Figure 5A:
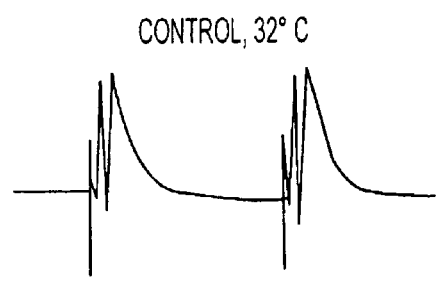
FIGS. 5A–5F. Evoked potentials were reversibly diminished by cooling. A bipolar electrode was used to stimulate perforant path and the resulting orthodromic extracellular field potential was detected in the dentate granule cell layer.
Figure 5D:
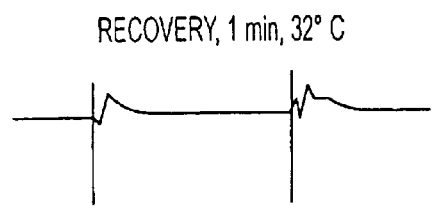
Figure 5B:
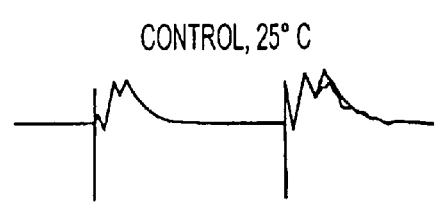
Figure 5E:
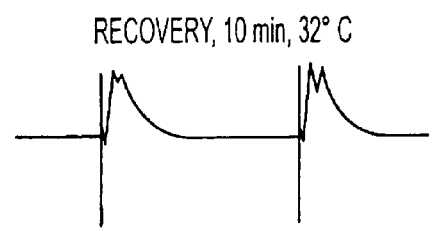
Figure 5C:
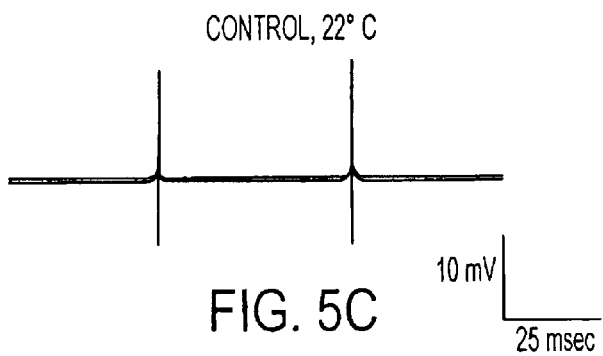
Figure 5F:
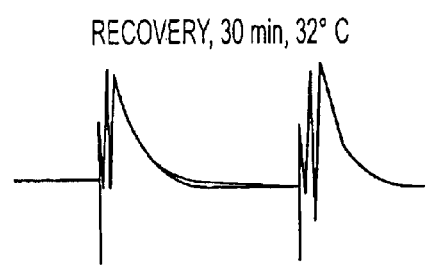

Since it was possible that cooling would injure the slices, we investigated the effect of cooling on dentate granule cell field potentials elicited by 100 μsec perforant path stimulation (ten slices), averaging five evoked responses for each condition. Cooling to 22° C. virtually eliminated the population spike in all slices (3.6±7.7% of control amplitude) (FIGS. 5B AND 5C; FIG. 5A illustrates a 32° C. control signal). Recovery was partial ten minutes after rewarming (50.6±28.6% of control) and complete by 30 minutes (103.8±41.2%) (FIG. 5). The 30 minute delay until full recovery correlates well with the reduced seizure probability in 4-AP-treated slices after cooling (FIG. 2C and 3).

Figure 6:
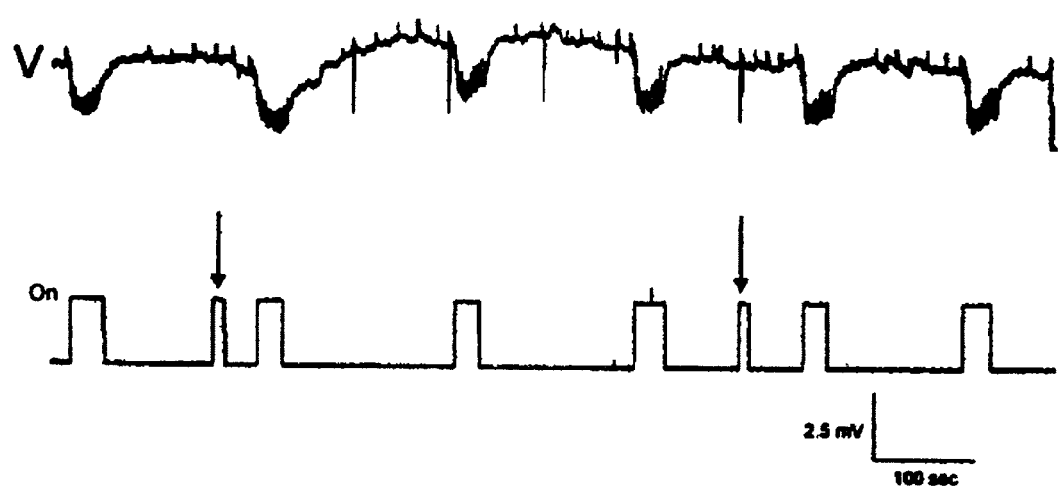
FIG. 6. Sample seizures were recorded onto DAT tape and played back later into our data acquisition system running the seizure detection program. The software correctly identified all six seizures in this record and continued to trigger the TTL output until the seizure activity stopped. The program also identified two brief bursts as seizures (arrows).

It was difficult to uniformly trigger the Peltier device at an identical latency from the onset of each seizure discharge. We, therefore, developed a program that was capable of generating a TTL pulse when it detected spikes that reached a frequency threshold that could be set for an individual slice. When we tested this program with data stored on tape, we found that it reliably detected bursting and produced a TTL pulse that lasted for the duration of the paroxysmal activity (FIG. 6). The program was sensitive enough to detect some brief, self-limited bursting so it is not absolutely specific for seizure discharges. When our program was used to process electrical activity on line in two slices, it reproducibly identified seizure discharges and automatically activated the Peltier device (FIGS. 7A AND 7B). In the first slice, the software detected nine seizures, which were stopped 2.1±0.6 sec after the Peltier was triggered (FIGS. 7A AND 7B). In the second slice 25 seizures terminated 3.7±1.0 sec after Peltier activation.

In vivo Cortical Cooling

Cooling a 600 μm thick slice with the Peltier device is relatively easy, since the slice generates little heat. In order to determine whether our Peltier would be able to focally cool human neocortex in vivo, we tested it on the neocortex of an anesthetized newborn pig. In these experiments, the Peltier was glued to the end of a brass rod and positioned flat against the exposed cortex with a micromanipulator. Peltier current was 0.4–0.5 amps. A thermocouple thermometer was then advanced with a second manipulator from the side of the Peltier toward its center. Baseline cortical temperature was about 36° C. When the angle between the thermometer and the cortex was 20°, the temperature decreased to 24.6° C. at a point 3.8 mm from the edge of the Peltier and 1.4 mm from the cortical surface (FIG. 8). When the thermometer was angled more steeply into cortex (50°), the temperature went down to 30.6° C. at a point 2.6 mm from the edge and 3.1 mm from the surface (FIG. 8).

Discussion

Our experiments demonstrate that cooling can very rapidly abolish seizure-like activity in vitro. Work from several other laboratories had previously shown that cooling would diminish paroxysmal activity, but the cortex was gradually cooled over several minutes in these experiments, so the seizures did not terminate instantly (7, 8, 9). Other investigators have also shown that in vitro bursting is influenced by slice temperature, but these experiments did not examine the effect of rapid temperature changes on paroxysmal activity (16). We recognize that our results are preliminary, in that they were obtained in a very artificial in vitro preparation that lacks many of the features of human epilepsy. Nonetheless, we believe there are several valuable conclusions from these experiments.

First, it is possible to rapidly cool mammalian cortex and stop seizures without producing irreversible damage. We were able to cool slices as low as 22° C. and still get complete return of field potentials. At least two clinical papers have already demonstrated that cooling the human brain is an effective antiepileptic strategy. Thirty years ago, Vastola and colleagues (17) showed that systemic hypothermia could help terminate medically refractory status epilepticus. A more recent report shows the benefit of local application of cold saline in controlling seizures induced during cortical mapping (18). The precise magnitude of temperature reduction that will be required in vivo is uncertain, but we measured a temperature decrease of only 0.2±1.2° C. between Peltier activation and seizure termination in the two slices in which the seizures were automatically detected. Of course, this may represent an underestimate, since the temperature detected by the thermocouple inserted into the top of the slice probably does not reflect the greater temperature reduction at the bottom of the slice. This could account for the observation that cooling in the first slice was actually detected 0.9 sec after seizure termination.

Second, it may be possible to use small Peltier devices to cool cortex in vivo, since the depth of human neocortex varies from about 1.5–4.5 mm, close to the depth we were able to cool in the newborn piglet cortex. At these depths, the recorded temperature was close to the slice temperature that effectively terminated seizures. Furthermore, a Peltier with a larger surface area could be employed to cool to a greater cortical depth.

Third, it is not unrealistic to imagine terminating seizures close to their onset, prior to motor manifestations and certainly before secondary generalization. There are now algorithms that can accurately predict seizure onset in data sets obtained from human depth electrode recording (19, 20). Pairing these algorithms with cooling appears to be a realistic goal. However, for the moment, much simpler spike detection algorithms work well in vitro where the interictal spike frequency is extremely low. Fourth, the efficacy of the cooling must be independent of any electric field effects, since there was no antiepileptic effect when the chip was not directly contacting the slice.

We have made no attempt to determine the exact anticonvulsant effect of cortical cooling. There are likely multiple mechanisms by which cooling reduces cortical excitability, including reduction of transmitter release and alteration of activation and inactivation kinetics of voltage-gated ion channels (15, 21).

There are obviously important problems in extending our work to in vivo epilepsy models and ultimately human epilepsy. We do not know the precise temperature that will be required in vivo, the volume of tissue that will have to be cooled, the optimal size of the Peltier device, and the necessary duration of cooling. Moreover, the recurrence of seizures with slice warming is worrisome, but not totally unexpected, since the epileptogenic insult (4-AP) had not yet been eliminated. We did not observe rebound hyperexcitability or spontaneous bursting when we examined the reversibility of cooling in slices not exposed to 4-AP, supporting the idea that the rebound was a result of continuous 4-AP exposure. While the delayed return of normal evoked responses may complicate translating our findings to seizures in vivo, it could account for the reduced likelihood of seizures in normothermic slices that had previously been cooled. This suggests a potentially beneficial, longer lasting, antiepileptic effect of cooling.

We are optimistic that these devices can be appropriately configured to influence the duration and frequency of seizures in vivo. We have completed a preliminary set of experiments in a model of focal neocortical epilepsy in rats induced by a microinjection of 4-AP and found that cooling the neocortex with a Peltier device can rapidly terminate electrical seizures (S. M. Rothman, unpublished). These experiments still require additional work, but the early results are encouraging.

Ultimately, it will be necessary to optimize heat sinks to fully exploit the potential benefits of these small cooling devices. While it is unrealistic to expect that totally implantable Peltier devices will soon be used for the chronic therapy of focal epilepsy, it should be possible to develop implantable subdural grids with an array of Peltier devices adjacent to recording electrodes as shown in FIG. 14. In FIG. 14, the array is shown generally comprising many individual Peltier devices 100 (each including a thermocouple and monopolar EEG electrode) located on a heat pipe substrate 102. A series of leads 104 run to a DC power source (not shown) for individual activation, while a corresponding lead from each device converges on the other pole 106 of the power supply. These might be helpful during invasive mapping, in anticipation of cortical resection, since rapid seizure suppression by focal cooling would confirm the site of origin of seizures. There are situations when a cortical abnormality identified by imaging does not accurately predict the actual origin of epileptic discharges, so temporary abolition of seizures by cooling could provide valuable localizing information (22). Temporary, focal cooling would also enable us to predict the deficits expected from resecting that portion of the cortex. Both of these uses would guide the location and extent of more conventional cortical resections for epilepsy, an important, and presently unmet, need in epilepsy surgery.

Materials and Methods for in vivo Control

Neocortical Seizure Model

We used a protocol approved by the Washington University Animal Studies Committee. At the start of the experiment, adult male Sprague-Dawley rats, 350–400 grams, were anesthetized with halothane and then placed on a heating pad in a stereotaxtic frame (David Kopf Instruments, Tujunga, Calif.) that allowed continuous halothane administration through a nose piece. We used halothane because other investigators have successfully produced prolonged seizures in halothane anesthetized rats[116]. The craniotomy was performed while the rat was breathing 4% halothane, which was reduced to <1% when we induced seizures. After infiltrating the skin with 2% lidocaine, we created a 5×10 mm cranial window over the anterior, left hemisphere using a dental drill (FIG. 10). The window extended medially to the sagittal sinus and 5 mm anterior and posterior to the coronal suture. After creation of the window, the dura was gently opened to allow drug injection. During the drilling, the skull was continuously irrigated with artificial cerebrospinal fluid to prevent the underlying brain from overheating.

We wanted a model that reliably generated sustained, focal electrographic seizures in an anesthetized animal. We initially tried to produce seizures with focal injections of the convulsants picrotoxin and bicucculine, but were unable to get consistent results. We switched to 4-aminopyridine (4-AP), which antagonizes the potassium channel responsible for fast action potential repolarization ($I_{K(A)}$) and has been used to trigger seizures in other in vitro and in vivo systems[115,117,118,119]. We injected 0.5 μl of a 4-AP solution (25 mM in artificial cerebrospinal fluid) using a commercial oocyte injection system (Drummond Scientific, Broomall, Pa.) coupled to a glass micropipette (tip diameter about 100 μm). The typical convulsant concentration of 4-AP is 50–100 μM in vitro, but we cannot be sure of our in vivo volume of distribution. We initially tried a 1 μl volume of injection, but cut back when animals developed refractory status epilepticus.

The injection system was mounted on a micromanipulator that allowed us to administer the 4-AP 0.5 mm below the surface of the motor cortex, at a position 2 mm anterior to the bregma and 2.5 mm from the midline (FIG. 10). The actual injection was carried out over 5 minutes, to minimize cortical trauma, and the pipette was left in place for 20 minutes to minimize leakage of the 4-AP. In several experiments, temperature and femoral artery pressure were continuously monitored and remained constant during seizures.

Electroencephalography (EEG)

We placed two screw electrodes symmetrically over each hemisphere and differentially recorded the EEG between the two, using standard amplifiers (FIG. 10). The EEGs were digitized and archived using standard hardware and software. We typically began EEG monitoring prior to injection of the 4-AP and continued throughout the entire experiment. Seizure onset was readily recognizable as an abrupt increase in EEG frequency and amplitude. Termination was not quite as clear cut, but the authors still closely agreed on seizure duration when 95 seizures were independently reviewed (R=0.966). All of the control seizure durations used to compare control and cooled seizures were corrected for the latency to seizure detection for that specific cooled group, so that the amount of time required to detect seizures and activate cooling would not unfairly bias our results. In our calculations, we took average values for seizure duration for each rat, so that rats with a larger number of seizures would not unfairly bias our results.

Focal Cooling

We focally cooled the neocortex with commercially available thermoelectric (Peltier) chips (Melcor, Trenton, N.J.). Two chips, each 3.5×3.5×2.4 mm were positioned together, glued to the end of a copper rod, and serially connected (FIG. 9B). The rod was a manipulator mount and an excellent heat sink. The Peltier chips were powered by an adjustable DC supply that limited current to <0.8 A. Temperature at the surface of the chips was monitored by attaching a 0.13 mm thermocouple (Omega Instruments, Stamford, Conn.). The output of the temperature controller was also digitized so that temperature could be observed simultaneously with the EEG. The copper rod was mounted in a three-axis micromanipulator and positioned so that the Peltier chips just touched the neocortical surface. In this configuration, the thermocouple reported the temperature at the interface between brain and chip.

Histology

In some of our experiments, the rats were sacrificed with an overdose of pentobarbital and perfusion-fixed with 100 ml of artificial cerebrospinal fluid, followed by 50 ml of 10% formalin. The formalin was preserved in 10% formalin. After thorough fixation, we cut sections (7 µm thick) that included the area around the injection site and corresponding contralateral neocortex and examined them with hematoxylin/esoin and Nissl staining for signs of necrotic injury, and TUNEL straining (TdT-meditated dUTP-biotin nick-end labeling) for evidence of apoptotic death (ApopTag Plus; Intergen, Purchase N.Y.)[121].

Results

We detected no seizures in animals after craniotomy alone or craniotomy followed by neocortical injection of artificial cerebrospinal fluid (CSF). However, within 30 minutes of 4-AP injection, non-cooled animals developed recurrent clinical (paw twitch) and electrographic seizures that remained for 2 hours. The corrected control seizure duration was 85.7±26.2 sec (n=66 seizures in 10 rats that never were cooled (FIGS. 11B AND 12A). All control seizure durations were corrected for the average latency between seizure onset and onset of cooling. This correction, which was 8.7±3.0 sec for all the cooling experiments, was necessitated by the delay between the start of the seizures and activation of the cooling. Although including this correction magnifies the differences in the length between cooled and uncooled seizures, the two populations would still be significantly different without correction.

In order to determine the stability of this model, we measured seizure duration over the two hour period after 4-AP injection, without any cortical cooling. We found that there was a small trend towards reduced seizure duration that did not alter the interpretation of our results (FIG. 12B).

We next examined the effect of rapidly cooling the cortex to 20–25° C., as quickly as possible after seizure onset and maintaining the cooling for 0.5 to 2 minutes. Cooling in this manner dramatically reduced the seizure duration (FIGS. 11C and 4A). Even if we grossly overcompensated for the gradual reduction in control seizure duration overtime (FIG. 12B) and assumed a value of 20±10 sec, a severe underestimate, the cooled seizures were still significantly shorter than control (p<0.05).

When cooling was discontinued, seizures sometimes recurred. We attributed this to the continued presence of the 4-AP at the seizure focus. Abrupt discontinuation of cooling did not provoke seizures in the absence of 4-AP, so there does not appear to be rebound hyperexcitability. The Peltier device had no effect on seizure duration when placed less than 0.5 mm from the cortical surface, but not in direct contact (FIGS. 11B AND 12A), arguing against a field effect independent of cooling.

Interestingly, when only some of the seizures were cooled, the remaining uncooled seizures were briefer than the seizures seen in control animals that had never been cooled (59.3±13.2 sec for 148 seizures in 10 animals that had been cooled v. 85.7±26.2 sec for 66 seizures in 10 control animals; p<0.01). This suggested that cooling might induce longer lasting changes in the excitability of the cortex. In order to prospectively test this hypothesis, we cooled the cortex of five animals for two, 2-minute periods, beginning 15 minutes after 4-AP injection, close to the anticipated start of seizures. After these two cooling periods, the cortex was allowed to rewarm and the EEG was recorded for 70 minutes. Seizure duration and frequency in this group of animals was compared to an identically treated control group of five rats that had not been cooled. Cooling reduced seizure duration from 68.7±18.7 sec to 42.8±13.9 sec (p<0.05) and seizure frequency (total number of subsequent seizures during 70 minute observation period) from 20.6±10.7 to 6.4±6.2 (p<0.05).

When we realized that the effect of rapid cooling described above might actually be influenced by prior cooling, we re-evaluated the effect of rapid cooling by comparing only the first cooled seizure in our experimental group to controls. We found that prior cooling could not account for the effect of rapid cooling. The average duration of the first cooled seizures was not significantly different from the average of all cooled seizures combined (FIG. 12A). Furthermore, the durations of the first through fifth cooled seizures were not significantly different, making prior cooling an unlikely confounding explanation for the rapid cooling results (FIG. 12C).

We were concerned that cooling the pial surface to 20°–25° C. would damage the underlying cortex. Therefore, we examined neocortex for evidence of infarction or selective neuronal injury after: 1. sham craniotomy; 2. cooling for two, 2 minute periods; 3. normothermic 4-AP injection; and 4. cooling for two, 2 minute periods and 4-AP injection. We performed routine hematoxylin/eosin and Nissl staining four-six hours and three days after seizures and saw no evidence of cortical infarction. The cooled/4-AP injected neocortex was completely indistinguishable from control (FIGS. 13A–13D). No TUNEL positive cells were detected in 8 slides independently reviewed by both authors (1 sham craniotomy; 2 cooled animals; 2 drug injected animals; 1 cooled, injected animal after 4 hours; and 2 cooled, injected animals after 3 days)(FIGS. 13A–13D). In order to establish that we could induce and identify injury with more extreme cooling, we produced a positive control by touching the cortex with a heat pipe in contact with a reservoir containing dry ice/ethanol (heat pipe temperature <−10° C. at tip). The neocortex that touched the pipe for two minutes showed a large number of shrunken neurons when Nissl stained and also demonstrated many TUNEL positive neurons after three days (FIG. 13D). We, therefore, believe that we would be able to detect significant cooling-induced cortical damage. We also had no difficulty detecting TUNEL positive cells in a mouse mammary tumor specimen known to contain cells undergoing apoptosis.

Discussion

The experiments described in this paper indicate that cooling holds promise as a strategy for controlling epilepsy. While the outcome of these experiments is clear cut, a number of details require elaboration.

First, we found it necessary to develop our own model of seizures, because established models were not appropriate for our experimental design. We required a model that quickly produced prolonged focal seizures in animals under general anesthesia. Because there is an eight second latency between seizure onset and identification, we would not have been able to detect a therapeutic effect of cooling if the seizures were too short. We also wanted the seizures to occur in anesthetized animals, because our present cooling technique requires that the head remain stable. Finally, we wanted to be able to trigger the seizures with a very focal application of convulsant, so we would know exactly where to position the Peltier device. The recent identification of potassium channel mutations in genetic human epilepsies, albeit generalized varieties, supports the use of a potassium channel antagonists in epilepsy models[121,122,123]. In our seizure model, the effect of cooling on seizure duration was dramatic, reducing the average seizure length by about 90%. While we were concerned that this effect could be due to the electrical field generated by the Peltier device, we saw no reduction of seizure duration when the Peltier was not allowed to directly touch the exposed cortex.

While our primary objective in these experiments was to determine whether rapid cooling could acutely abort seizures, we were pleased to see that cooling had a lasting effect on cortical excitability. After two periods of cooling, the frequency and duration of subsequent seizures was significantly reduced. This effect, which we observed in our in vitro experiments, suggests that cooling might have other anticonvulsive effects[115].

We were worried that cooling might injure underlying cortex, but so far have seen no evidence of structural damage. Stains looking for evidence of acute or delayed injury have been unable to distinguish control cortex from cortex exposed to acute seizures and cooling. We might have identified TUNEL-positive neurons in the 4-AP exposed cortex had we allowed more seizures or increased the observation period. However, our negative result is consistent with the clinical observation that morphological abnormalities do not always accompany intractable focal epilepsy.

There appear to be at least three situations where focal cooling using Peltier devices might improve the therapy of patients with intractable focal seizures. First, in the process of cortical mapping to identify the site of seizure origin, seizure suppression by focal cooling might provide confirmatory evidence prior to permanent surgical resection. Second, focal cooling during mapping could predict the potential cognitive consequences of resecting a region of neocortex. Third, an implantable cooling device that could be activated by a seizure detection or anticipation algorithm, might be an alternative to neocortical resection in some patients[124,125,126]. The first two potential uses would require adding an array of Peltier devices to the standard subdural recording grid already used in epilepsy surgery.

We recognize that there are other innovative approaches to focal therapy for epilepsy. Regional drug administration, implanted anticonvulsant-embedded polymers, and electrical stimulators have already had limited success in some model systems and patients[127-132]. While the problem of intractable focal epilepsy will not disappear soon, we are optimistic that advances in microelectronics and fabrication will improve therapeutic options for this devastating neurological disorder.

Parenthetical References Incorporated Herein by Reference:
1. Comair Y G, Choi H Y, Van Ness P. Neocortical Resections. In: Engel J Jr, Pedley T A, eds. *Epilepsy: A Comprehensive Textbook*. Philadelphia, Pa.: Lippincott-Raven, 1998: 1819–28.
2. Olivier A. Risk and benefit in the surgery of epilepsy: complications and positive results on seizure tendency and intellectual function. *Acta Neurol. Scand. Suppl.* 1988; 117:114–21: 114–121.
3. Olivier A. Surgery of Extratemporal Epilepsy. In: Wyllie E, ed. *The Treatment of Epilepsy*: Principles and Practice. Baltimore, Md.: Williams & Wilkins, 1997: 1060–73.
4. Goldring S. A method for surgical management of focal epilepsy, especially as it relates to children. *J. Neurosurg.* 1978; 49: 344–356.
5. Brooks V B. Study of brain function by local, reversible cooling. *Rev. Physiol. Biochem. Pharmacol.* 1983; 95:1–109.
6. Lomber S G, Payne B R, Horel J A. The cryoloop: an adaptable reversible cooling deactivation method for behavioral or electrophysiological assessment of neural function. *J. Neurosci. Methods* 1999; 86: 179–194.
7. Moseley J I, Ojemann G A, Ward A A J. Unit activity in experimental epileptic foci during focal cortical hypothermia. *Exp. Neurol.* 1972; 37: 164–178.
8. Reynolds J A, Ojemann G A, Ward J A. Intracellular recording during focal hypothermia of penicillin and alumina experimental epileptic foci. *Exp. Neurol.* 1975; 46: 583–604.
9. Lebovitz R M. Effects of temperature on interictal discharge at penicillin epileptogenic foci. *Epilepsia* 1975; 16: 215–222.
10. Hayward J N, Ott L H, Stuart D G, Cheshire F C. Peltier biothermodes. *American Journal of Medical Electronics* 1965; 4: 11–19.
11. Barbarosie M, Avoli M. CA3-driven hippocampal-entorhinal loop controls rather than sustains in vitro limbic seizures. *Journal of Neuroscience* 1997; 17: 9308–9314.
12. Park T S, Gonzales E R, Gidday J M. Platelet-activating factor mediates ischemia-induced leukocyte-endothelial adherence in newborn pig brain. *J. Cereb. Blood Flow Metab.* 1999; 19: 417–424.
13. Gidday J M, Park T S, Shah A R, Gonzales E R. Modulation of basal and postischemic leukocyte-endothelial adherence by nitric oxide. *Stroke* 1998; 29: 1423–1429.
14. Hill M W, de la Cruz M A M, Covey D F, Rothman S M. Effects of anticonvulsant lactams on in vitro seizures in the hippocampal slice preparation. *Epilepsy Research* 1999; 37: 121–131.
15. Shen K F, Schwartzkroin P A. Effects of temperature alterations on population and cellular activities in hippocampal slices from mature and immature rabbit. *Brain Res.* 1988; 475: 305–316.
16. Traynelis S F, Dingledine R. Potassium-induced spontaneous electrographic seizures in the rat hippocampal slice. *Journal of Neurophysiology* 1988; 59: 259–276.
17. Vastola E F, Homan R, Rosen A. Inhibition of focal seizures by moderate hypothermia. A clinical and experimental study. *Arch. Neurol* 1969; 20: 430–439.
18. Sartorius C J, Berger M S. Rapid termination of intraoperative stimulation-evoked seizures with application of cold Ringer's lactate to the cortex—Technical note. *J Neurosurg* 1998; 88: 349–351.
19. Osorio I, Frei M G, Wilkinson S B. Real-time automated detection and quantitative analysis of seizures and short-term prediction of clinical onset. *Epilepsia* 1998; 39: 615–627.
20. Martinerie J, Adam C, Le Van Quyen M et al. Epileptic seizures can be anticipated by non-linear analysis. *Nat. Med.* 1998; 4: 1173–1176.
21. Thompson S M, Masukawa L M, Prince D A. Temperature dependence of intrinsic membrane properties and synaptic potentials in hippocampal CA1 neurons in vitro. *Journal of Neuroscience* 1985; 5: 817–824.
22. Holmes M D, Wilensky A J, Ojemann L M. Hippocampal or neocortical lesions on magnetic resonance imaging do not necessarily indicate site of ictal onsets in partial epilepsy. *Ann. Neurol.* 1999; 45: 461–465.

Footnotes Incorporated Herein by Reference:
103. Brooks V B. Study of brain function by local, reversible cooling. Rev Physiol Biochem Pharmacol 1983;95:1–109

104. Lomber S G, Payne B R, Horel J A. The cryoloop: an adaptable reversible cooling deactivation method for behavioral or electrophysiological assessment of neural function [In Process Citation]. J Neurosci Methods 1999;86:179–194

105. Thompson S M, Masukawa L M, Prince D A. Temperature dependence of intrinsic membrane properties and synaptic potentials in hippocampal CA1 neurons in vitro. Journal of Neuroscience 1985;5:817–824

106. Shen K F, Schwartzkroin P A. Effects of temperature alterations on population and cellular activities in hippocampal slices from mature and immature rabbit. Brain Res 1988;475:305–316

107. Schiff S J, Somjen G G. The effects of temperature on synaptic transmission in hippocampal tissue slices. Brain Research 1985;345:279–284

108. Vastola E F, Homan R, Rosen A. Inhibition of focal seizures by moderate hypothermia. A clinical and experimental study. Arch Neurol 1969;20:430–439

109. Sartorius C J, Berger M S. Rapid termination of intraoperative stimulation-evoked seizures with application of cold Ringer's lactate to the cortex—Technical note. J Neurosurg 1998;88:349–351

110. Moseley J I, Ojemann G A, Ward A A J. Unit activity in experimental epileptic foci during focal cortical hypothermia. Exp Neurol 1972;37:164–178

111. Reynolds J A, Ojemann G A, Ward J A. Intracellular recording during focal hypothermia of penicillin and alumina experimental epileptic foci. Exp Neurol 1975;46:583–604

112. Traynelis S F, Dingledine R. Potassium-induced spontaneous electrographic seizures in the rat hippocampal slice. Journal of Neurophysiology 1988;59:259–276

113. Lebovitz R M. Effects of temperature on interictal discharge at penicillin epileptogenic foci. Epilepsia 1975;16:215–222

114. Hayward J N, Ott L H, Stuart D G et al. Peltier biothermodes. American Journal of Medical Electronics 1965;4:11–19

115. Hill M W, Wong M, Amarakone A et al. Rapid cooling aborts seizure-like activity in rodent hippocampal-entorhinal slices. Epilepsia 2000; 41:1241–1248

116. Hashizume K, Tanaka T. Multiple subpial transection in kainic acid-induced focal cortical seizure. Epilepsy Res 1998;32:389–399

117. Galvan M, Grafe P, ten Bruggencate G. Convulsant actions of 4-aminopyridine on the guinea-pig olfactory cortex slice. Brain Res 1982;241:75–86

118. Barbarosie M, Avoli M. CA3-driven hippocampal-entorhinal loop controls rather than sustains in vitro limbic seizures. Journal of Neuroscience 1997;17:9308–9314

119. Mihaly A, Joo F, Szente M. Neuropathological alterations in the neocortex of rats subjected to focal aminopyridine seizures. Acta Neuropathol (Berl) 1983;61:85–94

120. Gavrieli Y, Sherman Y, Ben Sasson S A. Identification of programmed cell death in situ via specific labeling of nuclear DNA fragmentation. J Cell Biol 1992;119:493–501

121. Biervert C, Schroeder B C, Kubisch C et al. A potassium channel mutation in neonatal human epilepsy. Science 1998;279:403–406

122. Charlier C, Singh N A, Ryan S G et al. A pore mutation in a novel KQT-like potassium channel gene in an idiopathic epilepsy family. Nat Genet 1998;18:53–55

123. Singh N A, Charlier C, Stauffer D et al. A novel potassium channel gene, KCNQ2, is mutated in an inherited epilepsy of newborns. Nat Genet 1998;18:25–29

124. Osorio I, Frei M G, Wilkinson S B. Real-time automated detection and quantitative analysis of seizures and short-term prediction of clinical onset. Epilepsia 1998;39:615–627

125. Martinerie J, Adam C, Le Van Quyen M et al. Epileptic seizures can be anticipated by non-linear analysis. Nat Med 1998;4:1173–1176

126. Le Van Q M, Martinerie J, Baulac M et al. Anticipating epileptic seizures in real time by a non-linear analysis of similarity between EEG recordings. NeuroReport 1999;10:2149–2155

127. Stein A G, Eder H G, Blum D E et al. An automated drug delivery system for focal epilepsy. Epilepsy Res 2000;39:103–114

128. Boison D, Scheurer L, Tseng J L et al. Seizure suppression in kindled rats by intraventricular grafting of an adenosine releasing synthetic polymer. Exp Neurol 1999;160:164–174

129. Schiff S J, Jerger K, Duong D H et al. Controlling chaos in the brain. Nature 1994;370:615–620

130. Gluckman B J, Neel E J, Netoff T I et al. Electric field suppression of epileptiform activity in hippocampal slices. Journal of Neurophysiology 1996;76:4202–4205

131. Jerger K, Schiff S J. Periodic pacing an in vitro epileptic focus. Journal of Neurophysiology 1995;73:876–879

132. Velasco M, Velasco F, Velasco A L et al. Subacute electrical stimulation of the hippocampus blocks intractable temporal lobe seizures and paroxysmal Egg activities, Epilepsia 2000;41:155–169

What is claimed:

1. A system for treating a patient having epilepsy which manifests in the form at intractable focal seizures, wherein a plurality of focal sites that are the source of said seizures have been located and mapped, said focal sites being located on a brain's neocortical surface, said system comprising:

an implantable subdural grid consisting of an array of cooling devices;

means for establishing direct physical contact between said focal sites and said cooling devices;

a plurality of recording electrodes, wherein at least one recording electrode is adjacent each said cooling device; and means for activating said cooling devices according to signals received from said recording electrodes, thereby cooling an appropriate focal site to abort the intractable focal seizure.

* * * * *